(12) United States Patent
Samson et al.

(10) Patent No.: US 10,228,357 B2
(45) Date of Patent: Mar. 12, 2019

(54) EGG FLAT IDENTIFICATION SYSTEM, AND ASSOCIATED METHOD

(71) Applicant: Zoetis Services LLC, Florham Park, NJ (US)

(72) Inventors: William Douglas Samson, Durham, NC (US); John Hilbert Hebrank, Durham, NC (US)

(73) Assignee: Zoetis Services LLC, Parsippany, NJ (US)

( * ) Notice: Subject to any disclaimer, the term of this patent is extended or adjusted under 35 U.S.C. 154(b) by 144 days.

(21) Appl. No.: 15/206,372

(22) Filed: Jul. 11, 2016

(65) Prior Publication Data

US 2017/0016871 A1    Jan. 19, 2017

Related U.S. Application Data

(60) Provisional application No. 62/192,112, filed on Jul. 14, 2015.

(51) Int. Cl.
| | |
|---|---|
| *G01C 9/00* | (2006.01) |
| *G01C 17/00* | (2006.01) |
| *G01C 19/00* | (2013.01) |
| *G01D 1/00* | (2006.01) |
| *G06F 15/00* | (2006.01) |
| *G06M 11/04* | (2006.01) |

(Continued)

(52) U.S. Cl.
CPC ........... *G01N 33/085* (2013.01); *A01K 43/04* (2013.01); *A01K 45/007* (2013.01)

(58) Field of Classification Search
CPC ... G01N 33/085; A01K 45/1007; A01K 43/04

USPC ................................................. 702/127, 150
See application file for complete search history.

(56) References Cited

U.S. PATENT DOCUMENTS

| | | | |
|---|---|---|---|
| 5,900,929 A | 5/1999 | Hebrank et al. | |
| 6,234,320 B1 * | 5/2001 | Hebrank | G01N 33/085 |
| | | | 209/51 |

(Continued)

FOREIGN PATENT DOCUMENTS

| | | | |
|---|---|---|---|
| WO | WO 93/01710 | * | 2/1993 |
| WO | WO 2010/095935 A1 | | 8/2010 |

OTHER PUBLICATIONS

PCT International Search Report and Written Opinion, International Filing Date Jun. 29, 2016; International Application No. PCT/US2016/039966, dated Sep. 30, 2016.

*Primary Examiner* — Michael P Nghiem
(74) *Attorney, Agent, or Firm* — Scott C. Mayhew (57) ABSTRACT

An egg flat identification system for identifying an egg flat among a collection of egg flats is provided. Such a system includes a first measurement device configured to determine a first measurement of a plurality of eggs carried by an egg flat. A processor is in communication with the first measurement device. The processor is configured to receive the first measurements from the first measurement device. A second measurement device is configured to determine a second measurement of the eggs in the collection of egg flats. The second measurement device is in communication with the processor such that the processor is capable of receiving the second measurements. The processor compares the second measurements with the first measurements so as to identify a respective egg flat among the collection of egg flats.

12 Claims, 5 Drawing Sheets

(51) Int. Cl.
*G01N 33/08* (2006.01)
*A01K 43/04* (2006.01)
*A01K 45/00* (2006.01)

(56) References Cited

U.S. PATENT DOCUMENTS

| | | | |
|---|---|---|---|
| 2002/0157613 A1* | 10/2002 | Phelps | A01K 45/00 |
| | | | 119/6.8 |
| 2006/0038978 A1 | 2/2006 | Zweig et al. | |
| 2006/0156989 A1* | 7/2006 | Hebrank | A01K 45/007 |
| | | | 119/6.8 |
| 2007/0024844 A1* | 2/2007 | Hebrank | G01N 33/085 |
| | | | 356/53 |
| 2015/0138535 A1* | 5/2015 | Walukas | G01N 33/085 |
| | | | 356/51 |
| 2017/0029149 A1* | 2/2017 | Robert | B65B 23/08 |

\* cited by examiner

EGG FLAT IDENTIFICATION SYSTEM, AND ASSOCIATED METHOD

CROSS REFERENCE TO RELATED APPLICATION

This application claims the benefit of U.S. Provisional Patent Application No. 62/192,112, filed Jul. 14, 2015, which is expressly incorporated herein by reference in its entirety.

TECHNICAL FIELD

The present disclosure generally relates to egg processing devices and systems. More particularly, the present disclosure relates to a system for identifying an egg flat carrying a plurality of eggs through one or more processing stations, and an associated method.

BACKGROUND

In poultry hatchery management, it may be desirable to separate birds based upon various characteristics, such as gender, diseases, genetic traits, etc. For example, it may be desirable to inoculate male birds with a particular vaccine and inoculate female birds with a different vaccine. Sex separation of birds at hatch may be important for other reasons as well. For example, turkeys are conventionally segregated by sex because of the difference in growth rate and nutritional requirements of male and female turkeys. In the layer or table egg industry, it is desirable to keep only females. In the broiler industry, it is desirable to segregate birds based on sex to gain feed efficiencies, improve processing uniformity, and reduce production costs.

In some instances, such determination of the desired characteristic may be carried out prior to hatch by means (e.g., bioassay process) in which the results of the characteristic are delayed or otherwise not immediately known. That is, the testing method to identify the desired characteristic may require some minimal amount of time for the analysis to be completed. For example, bioassays may require several minutes to hours after sampling each egg until assay results are available. During the interval, sampled eggs contained in egg flats must be stored and later assay results must be associated to the respective egg flat that was sampled. Traditional tracking means such as bar codes, paint, marks on eggs, and radio-frequency (RFID) may present their own problems, wherein bar codes may peel off, paint or markings may be removed by egg flat washing, and RFID tags may be cost prohibitive due to the substantial quantity of egg flats circulating among a hatchery and its farms.

Accordingly, it would be desirable to provide a system capable of identifying an egg flat among a collection of egg flats so that information determined about the eggs may be accurately associated with the egg flat downstream in the overall process. Furthermore, it would be desirable to provide an associated method to identify an egg flat among a collection of egg flats.

BRIEF SUMMARY

The above and other needs are met by aspects of the present disclosure which, according to one aspect, provides an egg flat identification system. The system includes a first measurement device configured to determine a first measurement of a plurality of eggs carried by an egg flat in a collection of egg flats. A processor is in communication with the first measurement device. The processor being is configured to receive the first measurements from the first measurement device. A second measurement device is configured to determine a second measurement of the eggs in the collection of egg flats, the second measurement device being positioned downstream from the first measurement device. The second measurement device is in communication with the processor such that the processor is capable of receiving the second measurements. The processor is configured to compare the second measurements with the first measurements so as to identify a respective egg flat.

Another aspect provides a method of identifying an egg flat within a collection of egg flats. The method comprises conveying a plurality of egg flats through a first measurement device, each egg flat containing eggs. The method further comprises determining with the first measurement device a first measurement of a plurality of eggs carried by a respective egg flat. The method further comprises storing the first measurements of each egg flat using a processor. The method further comprises conveying the egg flats through a second measurement device configured to determine a second measurement of the eggs measured by the first measurement device, and comparing the second measurements with the first measurements so as to identify a respective egg flat.

Thus, various aspects of the present disclosure provide advantages, as otherwise detailed herein.

BRIEF DESCRIPTION OF THE DRAWINGS

Having thus described various embodiments of the present disclosure in general terms, reference will now be made to the accompanying drawings, which are not necessarily drawn to scale, and wherein:

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

Figure 1:
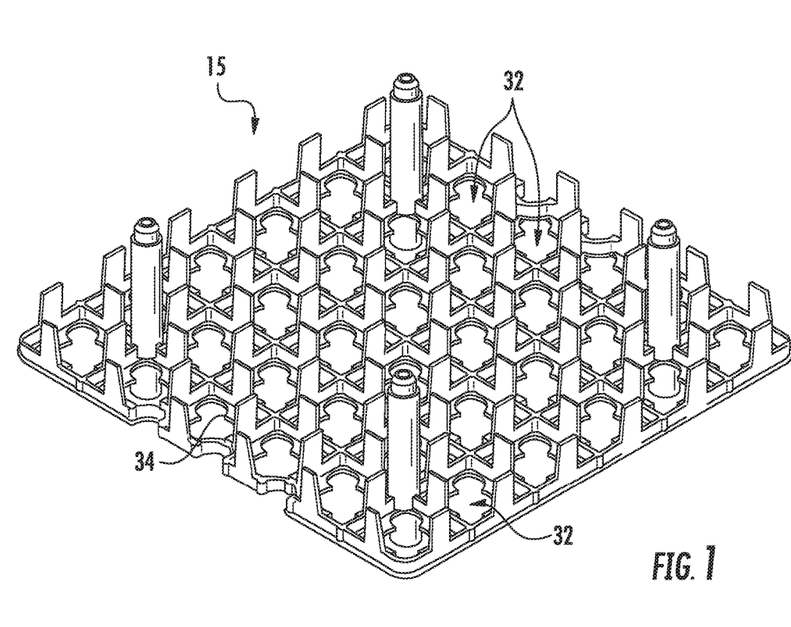
FIG. 1 is a perspective view of an egg flat capable of carrying a plurality of eggs in a vertical position.
Figure 4:
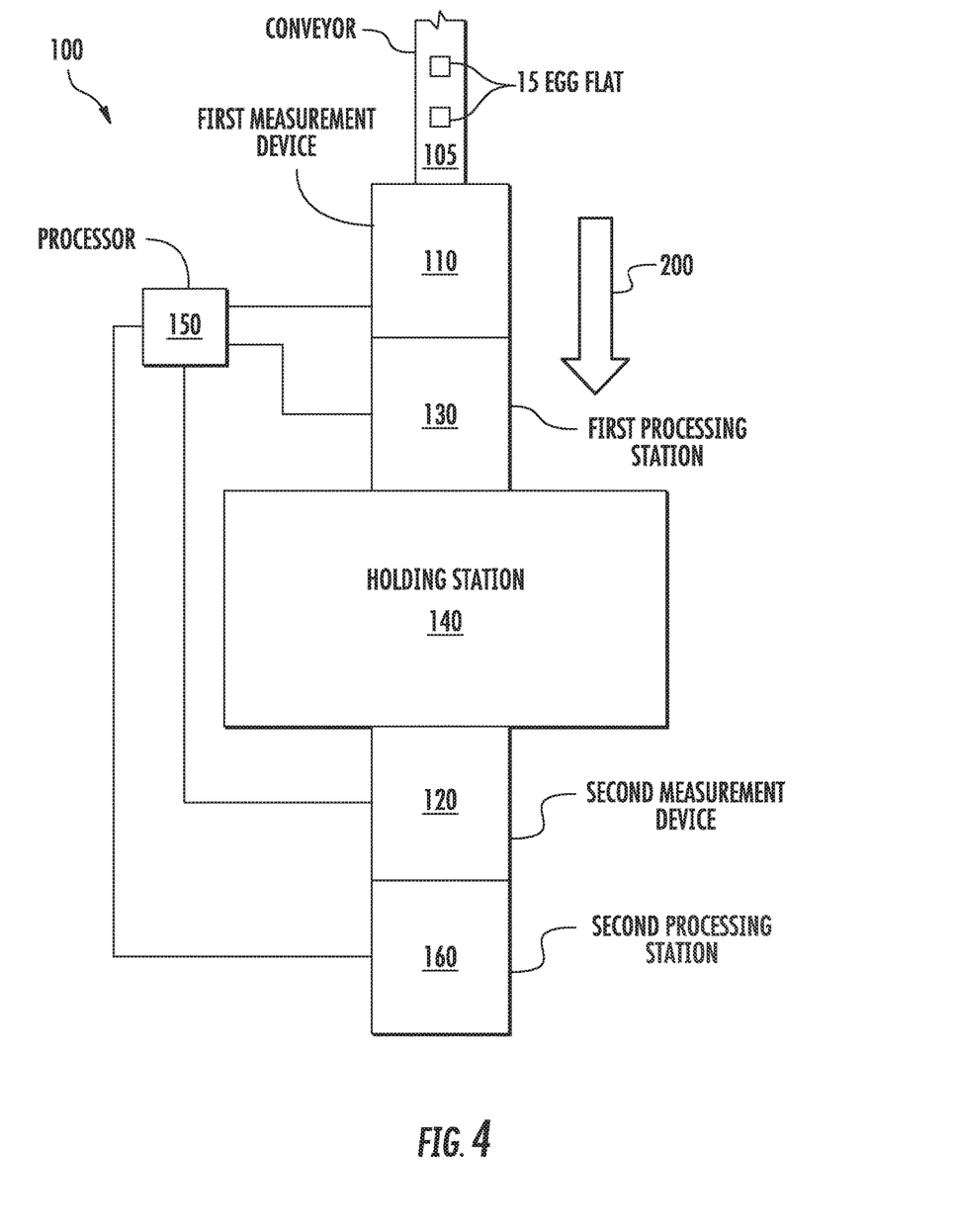
FIG. 4 is a schematic plan view of an egg flat identification system, according to one aspect of the present disclosure.

The apparatuses and methods of the present disclosure will now be described with reference to the figures. With initial reference to FIG. 4, illustrated in the figure is an exemplary system 100 for identifying an egg flat among a collection of egg flats. Egg flats are container- or tray-like structures used to hold a plurality of eggs as the eggs are subjected to various egg processing events such as, for example, incubation, sample withdrawal, and/or injection of a treatment substance. Egg flats may be arranged in many different shapes, sizes and geometric configurations, depending on the incubation equipment manufacturer. As shown in FIG. 1, an egg flat 15 may contain an array of pockets that are configured to support a respective plurality of eggs in a generally upright or vertical orientation.

The illustrated egg flat 15 includes a plurality of rows of pockets 32. Each pocket 32 may be configured to receive one end of a respective egg 20 (FIG. 2) so as to support the respective egg 20 in a substantially vertical position. Each pocket 32 of the illustrated egg flat 15 contains a plurality of tabs 34 that are configured to support a respective egg. The illustrated flat 15 holds a plurality of eggs 20 in a substantially upright position and is configured to provide external access to predetermined areas of the eggs 20.

As mentioned previously, it may be desirable to identify eggs as having an identifiable characteristic prior to hatch, such as, for example, embryo gender. In some instances, gender determination prior to hatch may be possible through a bioassay process, which may require several minutes to hours after sampling each egg until assay results are available. Thus, during the interval, sampled eggs contained in egg flats must be stored and later assay results must be associated to the respective egg flat that was sampled. Accordingly, the system 100 as disclosed herein is capable of providing such egg flat identification so that the bioassay results may be accurately associated downstream with the correct egg flat once the assay results become available and the egg flats are moved from storage.

According to one aspect of the present disclosure, the system 100 may include a first measurement device 110 and a second measurement device 120. One or more processors 150 or controller may be in communication with the first and second measurement devices 110, 120 such that measurements from the first and second measurement devices 110, 120 may be analyzed for egg flat identification. With reference to FIG. 4, in some instances, a conveyor 105 may be provided to move egg flats 15 through the system 100. The egg flats 15 may be manually or automatically loaded into the system 100 and then transported in a processing direction 200.

In some instances, the egg flat 15 may pass through the first measurement device 110 before encountering a first processing station 130 configured to process the eggs and being positioned upstream of the second measurement device 120. In other instances, however, the egg flat 15 may encounter the first processing station 130 prior to passing through the first measurement device 110. The first processing station 130 may include any device, apparatus, or system for processing an egg, such as, for example, an injection device for injecting a treatment substance (e.g., a vaccine), a sampling device for withdrawing/extracting a sample, or a removal device for removing eggs from the egg flat. In the example of a sampling device, the egg flat 15 may first pass through the first measurement device 110 so as to subject the eggs to a measurement, such as opacity using an egg candling device implementing optical measuring means. The egg flat 15 may then encounter the sampling device such that a sample of the egg (shell, tissue, blood, fluid, etc.) may be extracted for analysis. While the sample is being analyzed for some desired characteristic (e.g., gender), the egg flat 15 may be transported to a holding or storage station 140, awaiting results from the bioassay or diagnostic kit before being moved downstream to a second processing station 160, which may sort, remove, process, or treat (inject) the eggs according to the identified characteristic (e.g., sorted according to gender). In order to confirm the identity of a given egg flat 15 so as to confidently and accurately match the bioassay results with the correct egg flat 15, the second measurement device 120 may be positioned upstream of the second processing station 160 and prior to processing thereby. The measurements taken by the second measurement device 120 may be received by the processor 150 for comparison to the measurements taken by the first measurement device 110. This comparative process may be used to confirm the identification of an egg flat 15 such that the bioassay results transmitted to the processor 150 may then also be correctly transmitted to the second processing station 160 for appropriate processing.

According to some aspects, the first and second measurement devices 110, 120 may be egg candling devices configured to measure the opacity (i.e., a measurement related to the amount of light passing through an egg when illuminated by a light source) of the eggs carried in the egg flat 15. The light received by a detector for measurement of a given egg may be detected in raw form as voltage data, which may then be modified, standardized, corrected or otherwise manipulated into some unit of measure (arbitrary or otherwise). As is known to those familiar with poultry eggs, although egg shells appear opaque under most lighting conditions, they are in reality somewhat translucent, and when placed in front of a direct light, such as a candle or light bulb, the contents of the egg can be observed to a certain extent. Accordingly, various candling discrimination techniques may be used for the purpose of discriminating between live eggs and non-live eggs. Live eggs include eggs that were fertilized and contain a living embryo. Non-live eggs could be infertile eggs (sometimes referred to as "clear" eggs) or eggs with dead embryos. Compared to live eggs, infertile eggs allow more light to pass therethrough (particularly as compared to live eggs at later stages of incubation/embryo development) when illuminated since an embryo is not present.

In some instances, the egg candling device may implement a plurality of emitter-detector pairs through which the eggs pass such that an opacity measurement may be determined, as disclosed in U.S. Pat. No. 5,900,929 to Hebrank et al., which is incorporated herein in its entirety. The egg candling device may include an emitter assembly positioned above the conveyed egg flats 15 and a receiver assembly positioned below the conveyed egg flats. The egg candling device may scan eggs and identify the eggs as live or non-live (e.g., infertile). The emitter assembly may include a plurality of emitters that emit light through each egg and a respective receiver of the receiver assembly gathers the light passed through the egg. Light passing through each egg may be measured to determine whether the egg is live or non-live. Accordingly, information based on the measurements taken by the first and second measurement devices 110, 120 may be used to correctly identify an egg flat prior to a downstream processing event.

According to the present disclosure, the identification of an egg flat 15 may be accomplished by identifying or mapping a data pattern based on the measurements taken by the first and second measurement devices 110, 120. For example, the identification of an egg flat 15 may be accomplished by identifying or mapping the pattern of egg opacities on the egg flat. Non-contact measurement of opacity is advantageous because it avoids marking eggs or attaching anything to the egg flats, while using existing hardware to make the measurements. Further advantages include that no foreign materials are introduced into the hatchery or egg flat, no consumable cost, no threat to egg health, no risk of a change to egg flat geometry interfering with conveying, and one set of identification information made to incoming egg flats as a part of identifying infertile (clear) eggs to be selectively removed or not vaccinated. In some instances, the system 100 may also be capable of confirming that the orientation of the egg flat 15 is correct. That is, the information measured by the first and second measurement devices 110, 120 may be used to confirm that the egg flat 15 is oriented correctly.

Figure 2:
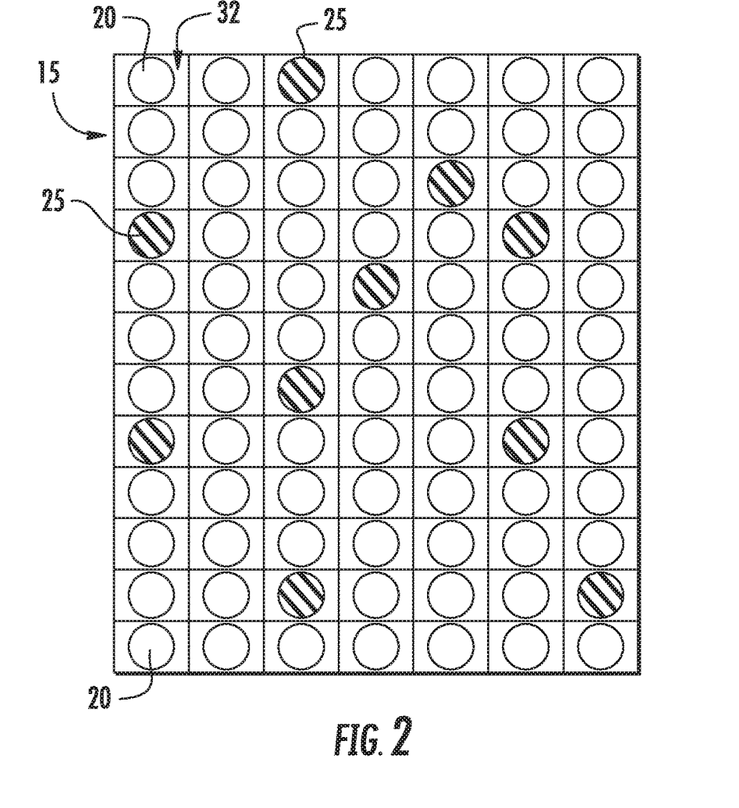
FIG. 2 is a schematic top view of an egg flat having a plurality of eggs positioned therein.
Figure 3:
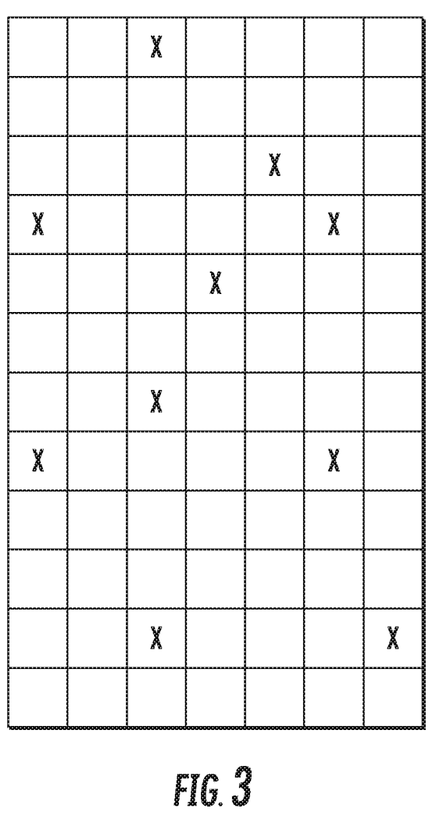
FIG. 3 is a pattern corresponding to an egg flat wherein the pattern is determined by identifying eggs within the egg flat as having a certain measurement quality, according to one aspect of the present disclosure.

In one aspect, an egg flat may be identified by the position of the infertile (clear) eggs on the egg flat. For example, as shown in FIG. 2, a plurality of infertile eggs 25 (shown with diagonal lines) may be identified by the first measurement device 110 (e.g., egg candling device). Such information regarding the infertile eggs and their position within the egg flat 15 may be received and stored by the processor 150. In some instances, the processor 150 may generate and store a data pattern, as shown in FIG. 3 for illustrative purposes (as corresponding to the egg flat 15 illustrated in FIG. 2 where "X" marks the position of an infertile egg), which may be used later to identify this particular among a collection or plurality of egg flats. In this regard, the measurements from the second measurement device 120 may be used for comparison to the measurements determined by the first measurement device 110. In some instances, the second measurements may also be patterned such that a comparison of patterns, as carried out by the processor 150, may be used to identify an egg flat. While the above example refers to patterning the infertile eggs of an egg flat, the converse may also be used wherein the eggs identified as live form the data pattern. Further, the pattern may be based upon any subset of eggs as identified by the first and second measurement devices 110, 120, such as, for example, infertile eggs, dead eggs, live eggs, etc.

While the example of FIG. 2 illustrates taking measurements of all eggs within the egg flat, it is also contemplated by the present disclosure that a measurement of a subset of the eggs in the egg flat may provide all information needed to confirm its identity by the second measurement device 120. That is, in some instances, fewer than all the eggs carried by the egg flat may be measured by the first and second measurement devices 110, 120 in order to form the pattern (or other identification technique) needed to identify the egg flat downstream. In some instances, measurement of a single row of eggs by the first measurement device 110 may be all that is needed to correctly identify the egg flat by the second measurement device 120.

For relatively error-free operation, when large numbers of egg flats are stored in the holding station 140 or extremely high fertility exists (i.e., very few infertile eggs), the value of egg opacity may be used to provide a more specific and error-free identification of the egg flats. Redundancy may allow correction for occasional opacity measurement errors or identifier channels that are loosely calibrated.

Figure 5:
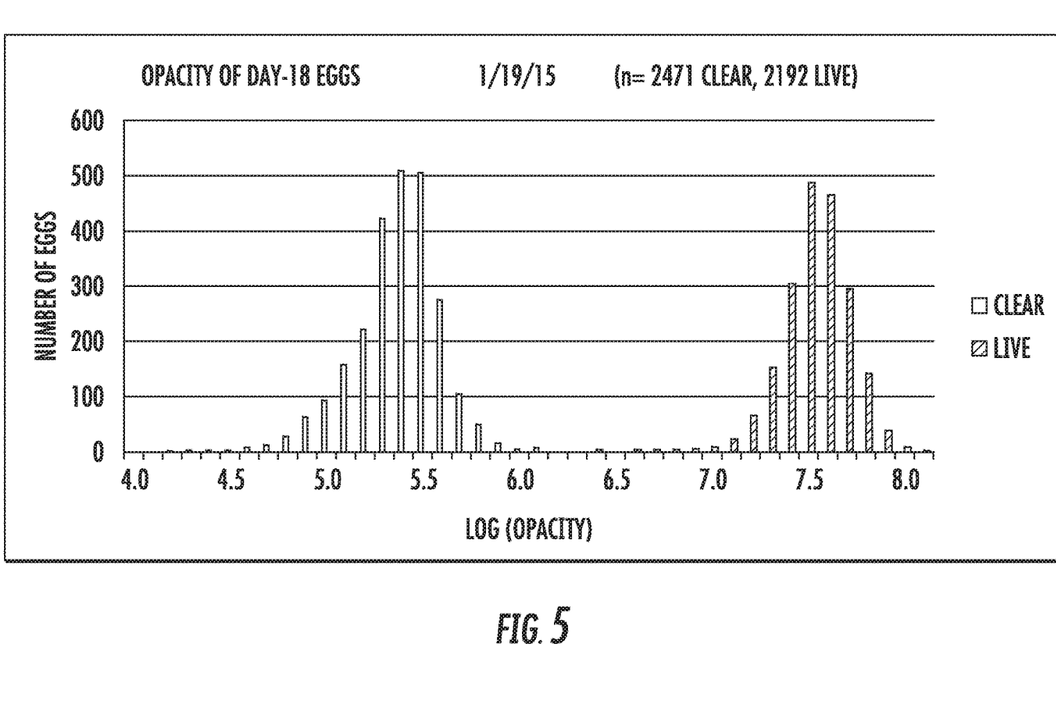
FIG. 5 is a graph illustrating the range of opacity values for live and infertile eggs at day eighteen of incubation.

As shown in FIG. 5, the opacity of live eggs may range over a factor of ten or more, with good repeatability of measurement. Similarly, infertile (clear) eggs may vary in opacity by a factor of ten or more, with values being repeatable, which may be attributed to variations in shell thickness. FIG. 5 is a plot of opacity for live and infertile (clear) eggs, illustrating the range of opacity values for live and infertile eggs at day eighteen of incubation. This plot illustrates a range of opacity for live eggs of about a factor of 10, or about 1.0 log (opacity). The plot further illustrates a range of opacity for infertile eggs as being a little more than a factor of 10, or about 1.0 log (opacity). This wide and stable variation among both live and infertile eggs may allow flats to be identified by the locations of brighter versus darker live or infertile eggs. Bin widths of 60% may be used for identification, which may typically be significantly larger than the variation among opacity senor channels and egg variation. The plot shows that bin widths of 60% (log (1.6) is 0.2) may provide four or five bins for live eggs and five bins for infertile eggs to define the opacity patterns on each egg flat. This finer gradation of opacity characterization may allow the egg flat identification system to function well with flocks of eggs having high fertility and, therefore, few infertile eggs and potentially more than one egg flat having a small number of infertile eggs in the same pattern.

In one example, the opacity values for all eggs on an egg flat may be determined by the first measurement device 110. The opacity values for all the eggs on the egg flat may be stored in a database. The egg flat may then go into storage while the bioassay incubates for minutes or hours. When the assay or diagnostic results are available, the egg flats may be removed one by one from the storage area and opacity values measured for all eggs on the egg flat by the second measurement device 120. A pattern matching algorithm may then determine which pattern of the egg flats in storage most closely matches the removed egg flat, and the assay results are accordingly associated with each egg.

According to one aspect, a pattern association algorithm may provide that the opacity of each egg on a flat be placed in a predetermined bin. The bins may have a width, for example, equal to a multiple of the variation in repetitive opacity measurements for eggs. For example, if repeatability of opacity measurement has a standard deviation of 15%, then each bin might be 50% wide giving bin edges of 1, 1.5, 2.25, 3.5 . . . . Thus, the opacity of each egg may be translated into one of fifty bin numbers for example. Small variations may cause some samples to be in one bin in the first measurement and an adjacent bin on the second measurement. Bin widths may be set so that being more than one bin apart between measurements is rare. Thus, an egg flat with eighty-four eggs may be represented by eighty-four numbers between one and fifty. In some instances, pockets 32 or egg flat positions that are missing eggs may also be in a bin (the missing bin, e.g., one bin past the clearest egg bin). For a group of egg flats that have been sampled (i.e., extraction of a sample from the egg), there may be a library of eighty-four numbers for each egg flat in the library. The order of the numbers may be the same as the position of the egg in the egg flat.

When an egg flat is to be linked with its assay results, opacity may again be measured by the second measurement device 120 for each egg on the egg flat and this data converted to a bin representation of eighty-four numbers between one and fifty. Then this pattern of eighty-four numbers may be compared to each egg flat in the archive and an error number generated for each column of this egg flat against each egg flat in the archive. In some instances, the worst column may be discarded and the error score for the other columns may be then generated for this egg flat against each egg flat in the library by a difference between each egg bin and the library egg at the same position. If opacity is in adjacent bins, then no error is assessed. The worst column may be discarded to avoid faulty adjustment of one identifier row or the occasional mis-read of an egg. In some instances, it may be desirable to square one less than the difference to underweight small errors. Similarly, there may be a maximum error assessed to account for the occasional misidentified egg. Also column data may be normalized based on a combination of statistics for each row.

According to further aspects of the present disclosure, the comparison between each egg and its counterpart may be done by calculating the ratio of their opacities. For example, if the opacity value is expressed as a log, then the ratio is the arithmetic difference of the two values. The error value between the two eggs may then be converted to a binary value according to whether the ratio is greater than a minimum (or the absolute value of the difference of the logs is greater than a fixed value). The error value may also be expressed as a numerical value where it is zero for small errors and then increases above a predetermined threshold.

Identifying a single egg flat as a match may be done if all but one row has zero errors (sum of the error values for all eggs in the row is zero). The first row of an egg flat may be compared against the first row of each other egg flat until error values are known for all comparisons. Then the error value of all the second rows may be calculated for all egg flats. Then the error values of all the third rows are compared for all egg flats that had an error value of zero for either the first or second row.

In the case of an egg flat with eighty-four pockets, with seven rows of twelve eggs, and 30,000 eggs (357 egg flats in the collection), a comparison of one row to all other first rows would be twelve times 357 times two summations (approximately 8,500 math operations). To calculate for all seven rows for the egg flats would be about 60,000 math operations (processed in a fraction of a second). In some cases the error value may be zero on the first egg flat examined, so no time will be consumed. In the case that no match shows zero errors, egg flats with minimal errors may be examined again with assumptions about missing rows of eggs. Statistical testing may be done with actual egg information and knowledge about opacity noise to determine the most efficient cut-on of the errors. This would be a tradeoff between noise from opacity errors and finding duplicate matches.

According to a further aspect of the present disclosure, a measurement algorithm may be accomplished when opacity is stored as a logarithm. Ratios may then be determined by subtraction of one opacity for another. A measure of goodness can be binary with differences less than a preset value given a value of one, and differences greater than a preset value given a zero. As previously describe, it may also be accomplished by eliminating a fixed number of eggs with the worst agreement and summing the remaining eggs, thus avoiding the situation where an egg is measured incorrectly by the opacity measuring system. Similarly, redundancy may be achieved by independently comparing columns to confirm the match.

According to another aspect of the present disclosure, an algorithm to develop a correspondence metric between two egg flats may use the logarithm of the opacity of each egg. Ratios may be determined by subtracting opacity values. A correspondence metric for two flats may be calculated as the root mean square (RMS) value of the opacity differences of eggs on one egg flat with the eggs in the same position on a second egg flat. The RMS function may treat positive and negative differences the same, while underweighting small differences. To avoid poor egg flat correspondence from an opacity misread of one or two eggs on an egg flat, the two eggs on the egg flat with the largest differences may be omitted from the RMS calculation. If the calculation needs to provide good correspondence data for situations where one identifier channel (emitter-detector pair) is defective, then the M eggs with the highest difference may be omitted from the RMS calculation (where M is the number of eggs per flat read by any one opacity channel). To decrease calculation time for large searches, the RMS value for the first row of eggs on each egg flat may be compared with the egg flat being tested as an initial screen followed by calculation for all eggs on each egg flat for egg flats with good correspondence of the first rows thereof.

According to one particular aspect, a method of generating a metric of correspondence for a pair of egg flats with each flat having N eggs is now described. A difference between each egg on one egg flat and the egg in same position on the second egg flat may be generated by subtracting the logarithm of the opacity of the first egg on the first egg flat from the logarithm of the opacity of the second egg on the second egg flat, which produces N differences. The highest M differences from N differences just generated may then be removed. In some instances, M may be set at one, two or a number equal to the number of eggs passing through one identifier channel. The metric of correspondence for the pair of flats may be generated by taking the square root of the sum of the squares of the N-M opacity differences calculated previously. When identifying which of a plurality of egg flats a particular egg flat matches, the lowest correspondence metric for the particular egg flat and each of the plurality of egg flats may be selected.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An egg flat identification system, comprising:
a first measurement device configured to determine a first measurement for each of a plurality of eggs carried by a target egg flat in a plurality of egg flats;
a processor in communication with the first measurement device, the processor being configured to receive the first measurements from the first measurement device and to generate and store a first data pattern according to the first measurements of the target egg flat;
a second measurement device configured to determine a second measurement of each of the eggs in an unidentified egg flat in the plurality of egg flats, the second measurement device being positioned downstream from the first measurement device, the second measurement device being in communication with the processor such that the processor is capable of receiving the second measurements so as to generate a comparative data pattern from the second measurements of the unidentified egg flat;
a holding station configured to store the plurality of egg flats awaiting a desired result, the holding station being disposed between the first and second measurement devices; and
wherein the processor is configured to compare the first data pattern with the comparative data pattern so as to identify the unidentified egg flat as the target egg flat among the plurality of egg flats.

2. A system according to claim 1, wherein the first and second measurements comprise opacity measurements of the eggs.

3. A system according to claim 1, wherein the first and second measurement devices comprise egg candling devices.

4. A system according to claim 1, further comprising a first processing station configured to process the eggs and positioned upstream of the second measurement device.

5. A system according to claim 4, further comprising a second processing station configured to process the eggs and positioned downstream of the second measurement device.

6. A system according to claim 1, wherein the first and second measurements are compared in at least one of a raw form and a modified form.

7. A method of identifying an egg flat within a plurality of egg flats, the method comprising:
conveying the plurality of egg flats through a first measurement device, each egg flat containing a plurality of eggs;
determining with the first measurement device a first measurement for each of a plurality of eggs carried by a target egg flat among the plurality of egg flats;
generating, via a processor, a first data pattern according to the first measurements of the target egg flat;
storing the plurality of egg flats at a holding station awaiting a desired result, wherein the holding station is downstream from the first measurement device;
conveying an unidentified egg flat from the holding station to a second measurement device configured to determine a second measurement of each of the eggs in the unidentified egg flat;
generating, via the processor, a comparative data pattern according to the second measurements of the unidentified egg flat; and
comparing the first data pattern with the comparative data pattern so as to identify the unidentified egg flat as the target egg flat among the plurality of egg flats.

8. A method according to claim 7, wherein determining the first and second measurements comprises determining first and second opacity measurements of the eggs using first and second egg candling devices, respectively.

9. A method according to claim 7, further comprising:
processing the eggs to determine a characteristic of each egg prior to conveying the plurality of egg flats through the second measurement device; and
processing the eggs downstream of the second measurement device according to the determined characteristic.

10. A method according to claim 9, wherein processing the eggs prior to conveying the plurality of egg flats through the second measurement device comprises extracting a sample from the eggs and assaying the sample to determine the characteristic of each egg.

11. A method according to claim 9, wherein processing the eggs downstream of the second measurement device comprises at least one of removing eggs from the plurality of egg flats according to the characteristic of each egg, sorting the eggs according to the characteristic of each egg, and treating the eggs according to the characteristic of each egg.

12. A method according to claim 9, wherein the characteristic is embryo gender.

* * * * *